United States Patent [19]

Höroldt et al.

[11] Patent Number: 4,686,097

[45] Date of Patent: Aug. 11, 1987

[54] PROCESS FOR THE REMOVAL OF THE RESIDUAL SULFURIC ACID FROM THE REACTION MIXTURE PRODUCED IN THE SULFOXIDATION OF PARAFFINS

[75] Inventors: Ernst Höroldt; Adam Urschel, both of Kelkheim, Fed. Rep. of Germany

[73] Assignee: Hoechst Aktiengesellschaft, Fed. Rep. of Germany

[21] Appl. No.: 719,267

[22] Filed: Apr. 2, 1985

[30] Foreign Application Priority Data

Apr. 5, 1984 [DE] Fed. Rep. of Germany ....... 3412844

[51] Int. Cl.⁴ .................. C01B 17/96; C01D 5/00; C07B 45/02; C07C 143/52
[52] U.S. Cl. .................. 423/520; 423/551; 260/504 S; 260/513 B; 260/513 T; 208/13
[58] Field of Search ............... 423/551, 520; 260/504 S, 513 B, 513 T; 208/13

[56] References Cited

U.S. PATENT DOCUMENTS

| | | | |
|---|---|---|---|
| 999,611 | 8/1911 | Walker et al. | 260/504 S |
| 1,673,045 | 6/1928 | Gray | 260/504 S |
| 1,996,692 | 4/1935 | Piotrowski et al. | 208/13 |
| 2,185,952 | 1/1940 | Rostler et al. | 208/13 |
| 2,940,936 | 6/1960 | Fike | 260/513 T |
| 3,461,159 | 8/1969 | Wendt et al. | 260/513 T |
| 4,183,867 | 1/1980 | Sekiguchi et al. | 260/513 T |
| 4,233,236 | 11/1980 | Kern et al. | 260/513 R X |
| 4,310,473 | 1/1982 | Springman et al. | 260/504 S |
| 4,518,537 | 5/1985 | Pistorius | 260/513 R |
| 4,557,873 | 12/1985 | Pistorius | 260/513 R |

FOREIGN PATENT DOCUMENTS

| | | | |
|---|---|---|---|
| 490751 | 12/1972 | U.S.S.R. | 423/520 |
| 611884 | 5/1976 | U.S.S.R. | 423/520 |

Primary Examiner—Andrew H. Metz
Assistant Examiner—William G. Wright
Attorney, Agent, or Firm—Connolly and Hutz

[57] ABSTRACT

Process for the removal of the residual sulfuric acid from the reaction mixture which has been obtained in the reaction of paraffin with sulfur dioxide, oxygen and water under irradiation by UV light and which has been freed from sulfur dioxide by degassing at an elevated temperature and from which the bulk of the sulfuric acid has been removed by concentration, by warming this concentrated product and adding as much of an alkali metal carbonate, peroxide, hydroxide, sulfate or sulfonate as is required to convert the residual sulfuric acid into an alkali metal bisulfate.

5 Claims, No Drawings

PROCESS FOR THE REMOVAL OF THE RESIDUAL SULFURIC ACID FROM THE REACTION MIXTURE PRODUCED IN THE SULFOXIDATION OF PARAFFINS

In the sulfoxidation of paraffins (n-alkanes) by means of sulfur dioxide, oxygen and water in the presence of UV light by the known light/water process, sulfuric acid is also formed in addition to the desired paraffinsulfonic acids (Chemie in unserer Zeit, 13 (1979), page 157 et seq.). In the course of the further working up, the sulfuric acid must therefore be removed be removed from the product phase which has been degassed and freed from the bulk of the unreacted paraffin. This removal of the sulfuric acid can be effected by neutralizing the product phase directly, for example by means of sodium hydroxide solution, and separating off the sodium sulfate produced. However, this method is disadvantageous, since in this case the whole of the sulfuric acid present is neutralized, which means a high consumption of alkali, and, in addition, a product which cannot be used further, namely sodium sulfate, is obtained.

Attempts are therefore made initially to separate off by other operations as large a fraction as possible of the free sulfuric acid from the product phase by phase separation. This can be effected by adding suitable solvents to the product phase, separation being achieved into an organic phase containing the alkanesulfonic acid and an aqueous phase composed of 15–25% strength sulfuric acid. A compilation of processes of this type is to be found in German Pat. No. 3,013,808. However, the sulfuric acid cannot thereby be removed quantitatively in these processes, and the residue remains in the end product after neutralization, in the form of sodium sulfate. Additionally, there is the disadvantage, inherent in all solvent processes, that an additional separation and working up of the solvent or solvent mixture is necessary.

In accordance with the process described in German Offenlegungsschrift No. 3,048,058 and German Offenlegungsschrift No. 3,210,573, it is also possible to remove the sulfuric acid from the product phase in the form of 20% strength sulfuric acid by means of organic salts, for example tributylammonium hydrogen sulfate or other amines. Problems arise, however, in the preparation of amine-free alkanesulfonic acids by this process.

A process for converting the sulfuric acid in the product phase into bisulfate by partial neutralization with sodium hydroxide solution is also known from German Offenlegungsschrift No. 2,855,849. A separation is achieved by distilling off water, if appropriate as an azeotrope with an added solvent, up to a stage where the bisulfate monohydrate is formed. The monohydrate is liquid at 58° C. so that, in theory, the salt can be drained off at 60° C. as the lower phase. It has been found in practice, however, that accurate adjustment to this point cannot be achieved under operating conditions. It is also possible to induce the formation, at 95° C., of a second phase composed of water, salt and free acid by adding a salt, for example sodium sulfate, to the product phase. However, in order to reach a usable, low residual content of sulfuric acid it is necessary to add an amount of salt corresponding to the weight of alkanesulfonic acid present.

In the sulfoxidation process as it is carried out on a large industrial scale (Chemie in unserer Zeit, 13 (1979), page 161), the product phase is concentrated in vacuo, without the addition of solvents, and water is removed by distillation together with a part of the paraffin. When it is concentrated, the distillation residue separates into 50–65% strength aqueous sulfuric acid and a concentrate of the following compositions: 35.0–40.0% of alkanesulfonic acid, 54.4–56.6% of paraffin, 4.0–5.5% of water and 1.6–3.1% of sulfuric acid.

This concentrate is neutralized with sodium hydroxide solution, and the residual paraffin is then removed by steam distillation. The alkanesulfonate melt which remains is formulated into flakes or aqueous solutions. The alkanesulfonates thus obtained contain a maximum of 4% of sodium sulfate at a concentration of 60% of active substance. While this low salt content does not generally cause problems, it can, however, have a disadvantageous effect in the case of certain specialities or in formulations of a higher concentration, since the viscosity of the alkanesulfonate increases as the sodium sulfate content rises, so that it is no longer certain that the product can be pumped and, at a fairly high sulfate content, separation of the product as the result of salt crystallizing out must always be expected.

The object of the present invention was, therefore, to reduce the residual content of sulfuric acid in the concentrates produced by this process and thus to prepare virtually salt-free alkanesulfonates. In so doing, essential process stages of the excellent and well-tried production process should not be altered.

The invention relates to a process for the removal of the residual sulfuric acid from the reaction mixture which has been obtained in the reaction of paraffin with sulfur dioxide, oxygen and water under irradiation with UV light and which has been freed from sulfur dioxide by degassing at an elevated temperature and from which the bulk of the sulfuric acid has been removed by concentration, by adding to this concentrated product phase at least as much of an alkali metal carbonate, peroxide, hydroxide, sulfate or sulfonate as is necessary to convert the residual sulfuric acid into an alkali metal bisulfate.

The starting point for the process according to the invention is the so-called concentrate as described above. An alkali metal salt of the type described above is added to this concentrate at a temperature of 20° to 120°, preferably 75° to 100° C., the amount thereof being what is required on the basis of the stoichiometric conditions to convert the whole of the sulfuric acid still present into an alkali metal bisulfate. Suitable salts of this type are, in particular, the sodium salts, such as sodium carbonate, sodium peroxide, sodium hydroxide, sodium sulfate and also the sodium alkanesulfonates themselves.

It is preferable to employ these salts in an anhydrous state, in order to avoid the formation of the bisulfate monohydrate, which is slimy and difficult to separate off. If aqueous solutions of the salts are taken, the yield of crystals and the rate of crystallization are effected adversely. Thus if only 30% strength sodium hydroxide solution is used, virtually no more salt crystallizes out. The reaction with sodium sulfate decahydrate does not take place in an optimal manner either. The salts are added in portions or continuously at a rate suited to the reaction, in order to prevent the occurrence of an excess of alkali, which can result in the formation of sodium sulfate, which is not desirable, or in partial neutralization of the alkanesulfonic acid. The temperature at which the salts are added to the concentrate depends essentially on the solubility of these salts. In general, the reaction is carried out at the temperatures which the concentrate is already at from the previous processing stage, i.e. at approx. 90°–95° C. The use of dilute aqueous or aqueous/alcoholic alkali solutions or alkali solutions diluted with another solvent is possible in accordance with the process according to the invention. In this case, it is necessary to remove from the reaction mixture, preferably by vacuum distillation, the water or solvent which interferes with the crystallization of the bisulfate.

In general, the use of a slight excess of alkali for partial neutralization, for example 1.5 times the stoichiometric amount, also does not interfere with the further course of the process. In this case a small amount of sodium sulfate then separates out in addition to the bulk of bisulfate.

The end of the partial neutralization when using a solid, anhydrous alkali metal salt is generally indicated by the fact that a clear solution is obtained, from which, after cooling below approx. 60° C., the hydrate-free bisulfate crystallizes out. The removal of the crystals is effected by a conventional means, for example via a centrifugal filter. After being freed from salt, the concentrate has a residual sulfuric acid content of about 0.3%. This concentrate is then processed in the customary manner, i.e. it is neutralized and the residual paraffin is expelled by means of superheated steam.

In principle, it is also possible to employ, as the precipitant, other compounds having an alkaline reaction which forms salts with the sulfuric acid which are insoluble in the concentrate, such as, for example, the carbonates of barium and calcium. However, the disadvantage of products of this type is that, if the reaction is not quantitative or if the sulfates formed are not quantitatively removed, interfering extraneous ions remain in the concentrate. Since alkanesulfonic acids prepared by other known sulfoxidation processes can also contain up to 10% of sodium sulfate in the end product, the present process can also be employed with advantage in these cases for the removal of the sulfuric acid, provided that a concentrate of analogous composition is present.

The percentages in the following examples are percentages by weight.

EXAMPLE 1

13,530 g of a sulfoxidation concentrate composed of 38.0% of alkanesulfonic acid, 2.2% of sulfuric acid, 4.9% of water and 55.0% of paraffin were heated to 95° C. in a 20 litre glass vessel. 160.98 g of sodium carbonate were introduced in portions at this temperature, in the course of 10 minutes and with stirring. The clear solution formed after the reaction was stirred for a further 60 minutes at 95° C. and was then cooled to room temperature. The salt which had crystallized out was removed at 4,500 rpm via a centrifugal filter lined with a filter cloth of pore width 5–10 μm. Potentiometric titration of the filtrate with a 0.1N solution of cyclohexylamine indicated a content of 38.0% of alkanesulfonic acid and 0.50% of sulfuric acid.

EXAMPLE 2

A solution of 10.92 g of potassium carbonate and 10.92 g of water was added dropwise at 92° C., in the course of 20 minutes and with stirring, to 842 g of sulfoxidation concentrate having the composition 39.7% of alkanesulfonic acid, 1.84% of sulfuric acid, 5.19% of water and 53.3% of paraffin. Stirring was continued for a further 30 minutes at this temperature, and the clear solution was then discharged into a crystallization vessel. The salt was filtered off with suction under a water pump vacuum and at room temperature via a G2 Schott glass filter of pore width 40–100 μm. The filtrate contained 40.8% of alkanesulfonic acid and 0.3% of sulfuric acid. 19.2 g of salt=81.9% of theory were isolated. The salt had a purity of 91.8%.

EXAMPLE 3

51.6 g of sodium peroxide were added at 90° C., within a period of 10 minutes and with stirring, to 709 g of a sulfoxidation concentrate composed of 38.6% of alkanesulfonic acid, 1.8% of sulfuric acid, 4.0% of water and 55.6% of paraffin. This reaction temperature was maintained for a further hour and, after cooling, the suspension was processed as described in Example 2. 38.0% of alkanesulfonic acid and 0.7% of sulfuric acid were found in the filtrate by titration.

EXAMPLE 4

21.97 g of sodium sulfate (anhydrous) were added at 95° C., in the course of 15 minutes and with stirring, to 824 g of sulfoxidation concentrate of the composition indicated in Example 1, and the mixture was kept at this temperature for 1 hour. It was cooled while being stirred. The finely crystalline precipitate could be removed by means of a G2 Schott glass filter. The filtrate contained 39.7% of alkanesulfonic acid and 0.7% of sulfuric acid. 35.5 g (84.2%) of salt were produced, corresponding to 80.5% of the theoretical amount.

EXAMPLE 5

49.8% of sodium alkanesulfonate (MW 275.5) were introduced, at the rate corresponding to its solubility, at 92° C. and with stirring into 893 g of sulfoxidation concentrate of the composition indicated in Example 1, and the reaction mixture was then heated for a further hour. After cooling it was possible to filter off the precipitated salt as described in Example 2. Titration of the filtrate indicated 42.5% of alkanesulfonic acid and 0.8% of sulfuric acid.

EXAMPLE 6

66 g of 8.5% strength sodium hydroxide solution were added dropwise at 80° C., in the course of 45 minutes and with stirring, to 854 g of sulfoxidation concentrate of the composition 35.9% of alkanesulfonic acid, 2.5% of sulfuric acid, 5.5% of water and 56.1% of paraffin. 84 g of a water/paraffin mixture composed of 90% of water were then distilled off from the reaction solution under a pressure of 93 mbar and at a temperature of 80°–85° C. After cooling to room temperature, the crystalline sodium bisulfate was filtered off from the bottom product. The filtrate contained 36.4% of alkanesulfonic acid and 0.7% of sulfuric acid. Salt amounting to 86% of theory and having a purity of 90% was isolated.

We claim:
1. A process for the removal of the residual by-product sulfuric acid from the concentrated mixture which contains alkanesulfonic acid and which (a) has been obtained from the reaction of paraffin with sulfur dioxide, oxygen and water under irradiation with ultraviolet light, (b) has been freed from sulfur dioxide by degassing at an elevated temperature and (c) has been freed, by concentration, from the bulk of the byproduct sulfuric acid, but not said residual byproduct sulfuric acid, which comprises adding to said concentrated mixture an alkali metal salt selected from an alkali metal carbonate, peroxide, hydroxide, sulfate or sulfonate, at a rate which provides partial neutralization of the residual sulfuric acid, thereby forming the alkali metal bisulfate, substantially without neutralizing the alkanesulfonic acid, and removing the alkali metal bisulfate from the alkanesulfonic acid.

2. The process as claimed in claim 1, wherein the alkali metal salt is added at a temperature of 20° to 120° C.

3. The process as claimed in claim 1, wherein the alkali metal salt is a sodium salt.

4. The process as claimed in claim 1, wherein an aqueous solution of the alkali metal salt is employed in order to form the bisulfate, which crystallizes out, and any of the water of this aqueous solution which interferes with the crystallization of the bisulfate is removed by distillation.

5. The process as claimed in claim 4, wherein the bisulfate which is formed and which crystallizes out, under crystallizing conditions, is substantially hydrate-free.

* * * * *